(12) United States Patent
Craig et al.

(10) Patent No.: US 6,707,047 B2
(45) Date of Patent: Mar. 16, 2004

(54) METHOD TO MEASURE HYDROGEN-BEARING CONSTITUENT IN A MATERIAL USING NEUTRON SPECTROSCOPY

(75) Inventors: Richard A. Craig, West Richland, WA (US); Mary Bliss, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/417,695

(22) Filed: Apr. 17, 2003

(65) Prior Publication Data

US 2003/0178573 A1 Sep. 25, 2003

Related U.S. Application Data

(62) Division of application No. 09/656,228, filed on Sep. 6, 2000, now Pat. No. 6,580,079.

(51) Int. Cl.⁷ .................. G01N 23/09; G01N 23/204
(52) U.S. Cl. .................. 250/390.04; 250/390.05; 250/390.11; 250/358.1
(58) Field of Search .............. 250/390.04, 390.05, 250/390.11, 358.1

(56) References Cited

U.S. PATENT DOCUMENTS 5,479,023 A * 12/1995 Bartle .............. 250/390.04

* cited by examiner

*Primary Examiner*—Constantine Hannaher
*Assistant Examiner*—Shun Lee
(74) *Attorney, Agent, or Firm*—Woodard, Emhardt, Moriarty, McNett & Henry LLP

(57) ABSTRACT

A non-destructive method for quantifying the hydrogen content or a hydrogen-bearing constituent in a material is based on the principle of moderating neutron spectroscopy. This technique is particularly suited for analyzing materials containing the high scattering/capture cross-section element of hydrogen. The method involves exposing a neutron moderator to a beam of radiation comprising neutrons and measuring thermal neutron intensities at a plurality of locations in the moderator. These measured intensities reflect the energy distribution of the beam of radiation incident upon the moderator. Thus, by measuring these intensities with the material present, and comparing these intensities to a model, to those of a composition standard(s), or combinations thereof, the hydrogen content of the material is quantified. Furthermore, the hydrogen-bearing constituent of the material is quantified by knowing or estimating the chemical or molecular structure of the material.

26 Claims, 8 Drawing Sheets

FIG. 6C

METHOD TO MEASURE HYDROGEN-BEARING CONSTITUENT IN A MATERIAL USING NEUTRON SPECTROSCOPY

The present application is a divisional of U.S. application Ser. No. 09/656,228 filed Sep. 6, 2000, now U.S. Pat. No. 6,580,079, the disclosure of which is incorporated by reference.

FIELD OF THE INVENTION

The present invention relates generally to innovations and improvements in the non-destructive quantitative analysis of material composition by measuring the change in energy spectrum of neutron radiation that has been transmitted through, or backscattered from, a material. More particularly, the present invention relates to a method for quantifying the amount of hydrogen or hydrogen-bearing constituent in a material using a source of radiation comprising neutrons or a combination of neutrons and gamma rays. "Gamma rays" used hereinafter include photons produced by changes in electron energy states of an atom (i.e., X-rays) in addition to photons produced by changes in energy states in the nucleus.

BACKGROUND OF THE INVENTION

There are numerous agricultural, commercial, industrial, geological and security applications requiring the non-destructive determination of the amount of a hydrogen-bearing constituent in a material. For example, there is a need to measure water or fat content in agricultural products (e.g., grain, soybeans, cottonseeds, meat, milk), measure steam quality, measure hydrogen content in fuels, and detect explosives.

Current non-destructive methods for determining composition using penetrating radiation include gamma ray absorptiometry and prompt or delayed gamma neutron activation analysis (PGNAA). Gamma-ray absorptiometry is exemplified by U.S. Pat. Nos. 2,992,332 and 4,168,431 and illustrated in a simplified manner in FIG. 1. The material 100 to be analyzed is exposed to an incident beam of radiation 110 comprising gamma rays from a radiation source 120 (hereinafter referred to simply as "source") whereby the reduced intensity of the transmitted beam 130 thereof is measured by a detector 140, such as an ionization chamber.

Figure 1:
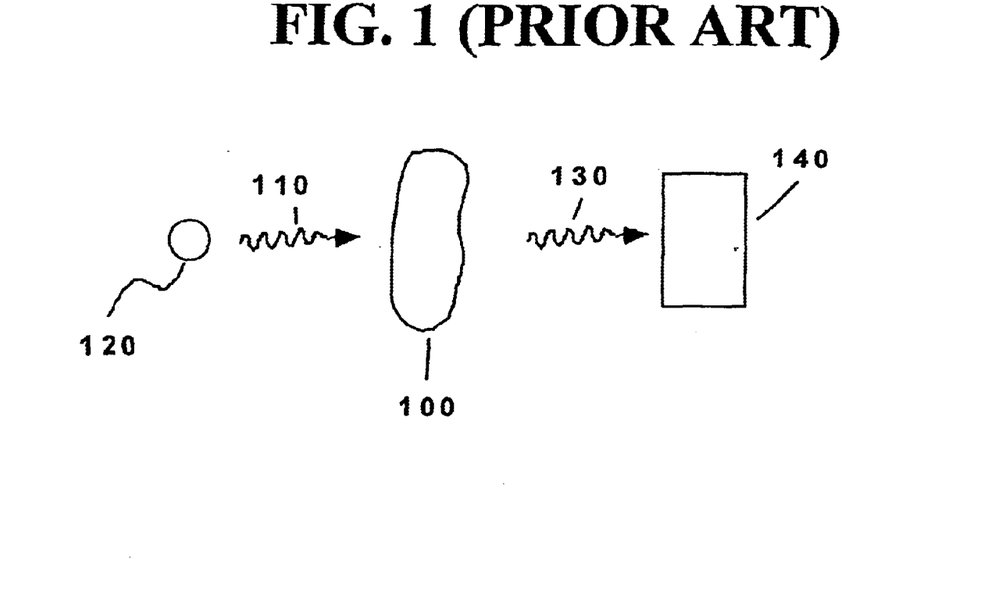
FIG. 1 (PRIOR ART) is a simplified schematic illustration of the prior art relating to composition determination using radiation absorptiometry.

In this method, the gamma rays give up some or all of their energy within the material 100 in three principal ways which are characterized as: the photoelectric effect, the Compton effect, and pair production effect. The photoelectric effect occurs when a gamma ray (<~0.1 MeV) strikes an electron in one of the orbits of an atom, dislodging it therefrom. The gamma ray gives up its entire energy to raising the kinetic energy of the electron (true absorption) equal to the gamma ray energy minus the binding energy of the electron. The Compton effect occurs when a gamma ray (>~0.1 MeV) also strikes an electron in one of the orbits, dislodging the electron from its orbit, but only a part of the gamma ray energy is used up, and the gamma ray itself is deviated from its path by the collision (scattering absorption). In the pair production effect, the gamma ray (>~1 MeV) is annihilated in the vicinity of the nucleus of the absorbing atom with the subsequent production of an electron and positron pair.

Another absorptiometric method for determining composition is exemplified by U.S. Pat. No. 5,479,023 which discloses a method of transmitting an incident beam of radiation 110 comprising different species (gamma rays and neutrons) from a source 120 through a material 100. A similar setup to that shown in FIG. 1 is used in this method except that the detector 140 also comprises a thermal neutron detector. In such absorptiometric methods, the transmitted radiation intensity measurements are typically analyzed with reference to known characteristic gamma ray and neutron attenuation coefficients and density properties.

It is important to note that measuring certain characteristics of the transmitted neutrons can provide different compositional information about the material 100 than that gained by measuring the gamma rays alone. This is based on the fact that neutrons interact with the constituents of the material 100 in a different manner than gamma rays. That is, the neutrons give up some or all of their energy in the material 100 by: elastic collision, inelastic collision, and radiative capture. Elastic collision occurs when the neutron shares its kinetic energy with a nucleus without exciting the nucleus. This is the primary mode of energy loss for neutrons as they are slowed or "moderated" to thermal energies by interaction with light nuclei (e.g., graphite or hydrogenous "moderators" such as water and polymers). Inelastic collision usually occurs with fast neutrons whereby the nucleus becomes excited upon collision, emits a gamma ray, and shares the remainder of the available kinetic energy with the scattered neutron. Radiative capture occurs when a neutron is absorbed to produce an excited compound nucleus which attains stability by emission of a gamma ray. Radiative capture is the basis of PGNAA whereby the gamma ray emission spectrum is analyzed to determine composition.

Figure 2:
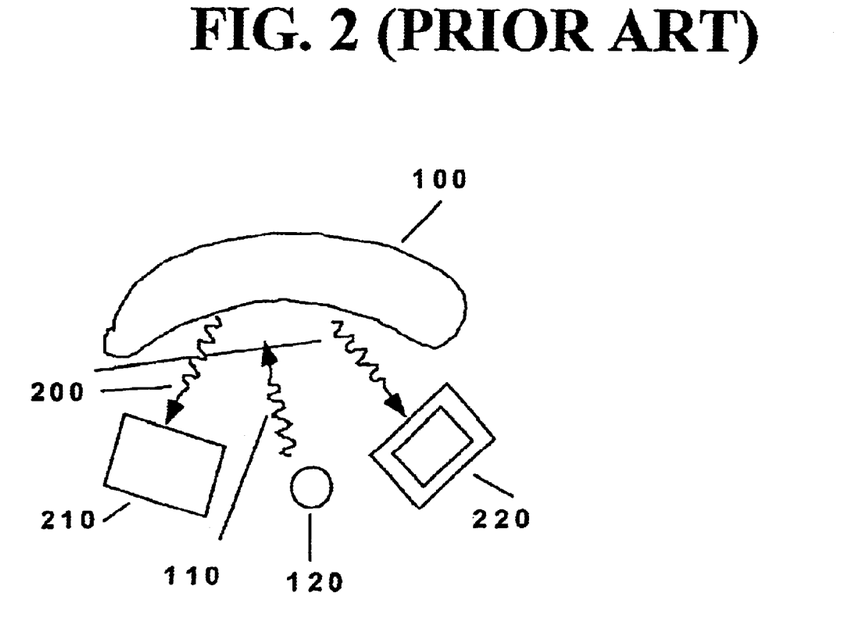
FIG. 2 (PRIOR ART) is a simplified schematic illustration of the prior art relating to composition determination using radiation backscattering and thermalization.

Another neutronic method for determining composition, disclosed in U.S. Pat. No. 5,327,773 and schematically illustrated in FIG. 2, utilizes a backscattering and thermalization technique. In this method, well known to practitioners of the geologic sciences, the density of steam (i.e., the material 100) in a conduit is measured by differentially measuring the thermal and epicadmium backscattered neutron radiation 200 generated by the incident beam of radiation 110 (from the source 120) interacting with hydrogen nuclei in the material 100. A first thermal neutron detector 210 and a second thermal neutron detector 220 (typically shielded with cadmium) are used in such a technique. A disadvantage of this method, however, is the length of the counting times associated with the inefficient detection of epicadmium neutrons.

In all of the aforementioned neutronic methods, however, the analyses do not utilize the great wealth of information contained in the changes in the multiple levels of energy in the neutron energy spectrum between the incident and transmitted, or backscattered, radiation resulting from the excellent neutron moderating property of hydrogen. Accordingly, there is an opportunity with the present invention to replace or improve current hydrogen analysis techniques by a more efficient neutron spectroscopic technique.

BRIEF SUMMARY OF THE INVENTION

The present invention is a non-destructive method for quantifying the amount of hydrogen or a hydrogen-bearing constituent in a material. The method is based on the principle of moderating neutron spectroscopy which is particularly suited for analyzing materials containing the high scattering/capture cross-section element of hydrogen. The method comprises the steps of exposing a neutron moderator to a beam of radiation comprising neutrons and measuring thermal neutron intensities at a plurality of locations in the moderator. These measured intensities reflect the energy distribution of the beam of radiation incident upon the moderator. Thus, by measuring these intensities with a material present, and comparing these intensities to a model, to those of a composition standard(s), or combinations thereof, the hydrogen content of the material is quantified. Furthermore, the hydrogen-bearing constituent of the material is quantified by knowing or estimating the chemical or molecular structure of the material.

The subject matter of the present invention is particularly pointed out and distinctly claimed in the concluding portion of this specification. However, both the organization and method of operation, together with advantages and objects thereof, may best be understood by reference to the following description taken in connection with accompanying drawings wherein like reference characters refer to like elements.

DETAILED DESCRIPTION OF THE INVENTION

The present invention utilizes the principle of moderating neutron spectroscopy as distinguishable from conventional time-of-flight neutron spectroscopy. Spectrometers based on moderating neutrons are spectrometers in the sense that their response (i.e., efficiency) is a function of the distribution of neutron energies. In one traditional type of moderating neutron spectrometer (Bramblett, R. L., Ewing, R. I., and Bonner, T. W., "A New Type of Neutron Spectrometer," Nuclear Instruments and Methods, 9, 1960, 1–12), a thermal neutron detector (i.e., a small lithium iodide scintillator) is placed at each center of a number of spheres of various diameters (i.e., 5 to 30 cm in diameter) made of a neutron moderating material (i.e., polyethylene). The competition between the neutron moderating and neutron capture properties of the moderator act to change the efficiency of the detector as the neutron energy changes. By measuring the thermal neutron count rate within each "Bonner's sphere" individually, an unfolding process provides information about the energy distribution of the incident neutrons.

More recently, the design, operation, and sensitivity of an improved moderating neutron spectrometer based on the same principle as Bonner's spheres was disclosed ("Spectroscopy Without a Spectrometer", M. Bliss, R. A. Craig, and D. S. Sunberg, Proc. SPIE Vol. 3180, p. 58–62, Third Pacific Northwest Fiber Optic Sensor Workshop, September 1997, Eric Udd; Chuck C. Jung; Eds. and Craig, R. A. and Bliss, M. "Predicted Performance of Neutron Spectrometers Using Scintillating Fibers," PNNL-13111, February 2000, both incorporated by reference herein). This improved spectrometer uses fiber-based thermal neutron detectors (such as that disclosed in U.S. Pat. No. 5,680,423, incorporated by reference herein) which allow simultaneous readout of multiple, geometrically equivalent, positions and greatly increase the measurement accuracy and efficiency of the spectrometer.

The present invention described herein uses one or more moderating neutron spectrometers in a variety of configurations to non-destructively quantify the amount of hydrogen or a hydrogen-bearing constituent in a material. As will be described in detail below, the spectroscopic method comprises the steps of exposing a neutron moderator to a beam of radiation comprising neutrons and measuring thermal neutron intensities at multiple locations in the moderator. These measured intensities reflect the energy distribution of the beam of radiation incident upon the moderator. Thus, by measuring these intensities after the radiation has interacted with a material, the hydrogen content of the material can be quantified by comparing these intensities to a model, to those of composition standard(s), or combinations thereof. Furthermore, the hydrogen-bearing constituent of the material is quantified by knowing or estimating the chemical or molecular structure of the material. It is understood that, while the primary focus of the description herein relates to a set of moderating neutron spectrometer configurations, the present invention should not be so limited, and operation of other embodiments will be readily apparent to those skilled in the art.

Figure 3A:
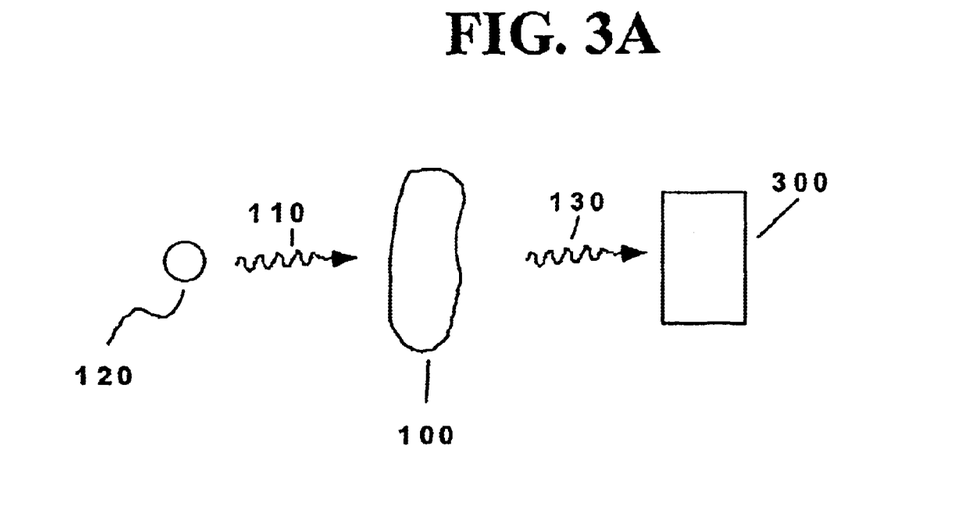
FIG. 3A is a simplified schematic illustration of an embodiment of the present invention whereby the radiation is transmitted through the material to the moderating neutron spectrometer.

FIG. 3A illustrates a simplified schematic of an embodiment of the present invention. In this embodiment, the material 100 to be analyzed is positioned between a source 120 and a moderating neutron spectrometer 300 (hereinafter referred to simply as "spectrometer"). As is known to those skilled in the art, shielding (not shown) is typically required proximate the source for configuring the geometry of the incident beam of radiation 110 and proximate the spectrometer 300 to shield noise (shielding is also good practice for personnel protection). In the present invention, the source 120 comprises a neutron source (e.g., a fissionable isotope, an ($\alpha$, n) source, a neutron generator, and combinations thereof) or a neutron and gamma ray source (e.g., a fissionable isotope, neutron generator and gamma ray emitting radioisotope, neutron generator and gamma ray generator, and combinations thereof). As is known to those skilled in the art of gamma ray absorptiometry discussed in the Background, measuring the attenuation of gamma rays that have passed through a material 100 provides information on the heavier constituents (e.g., N and O vs. H and C) and the physical form (e.g., thickness) of the material 100. In one embodiment of the present invention a fissionable isotope source, such as Cf-252, conveniently produces neutrons and gamma rays simultaneously.

Figure 3B:
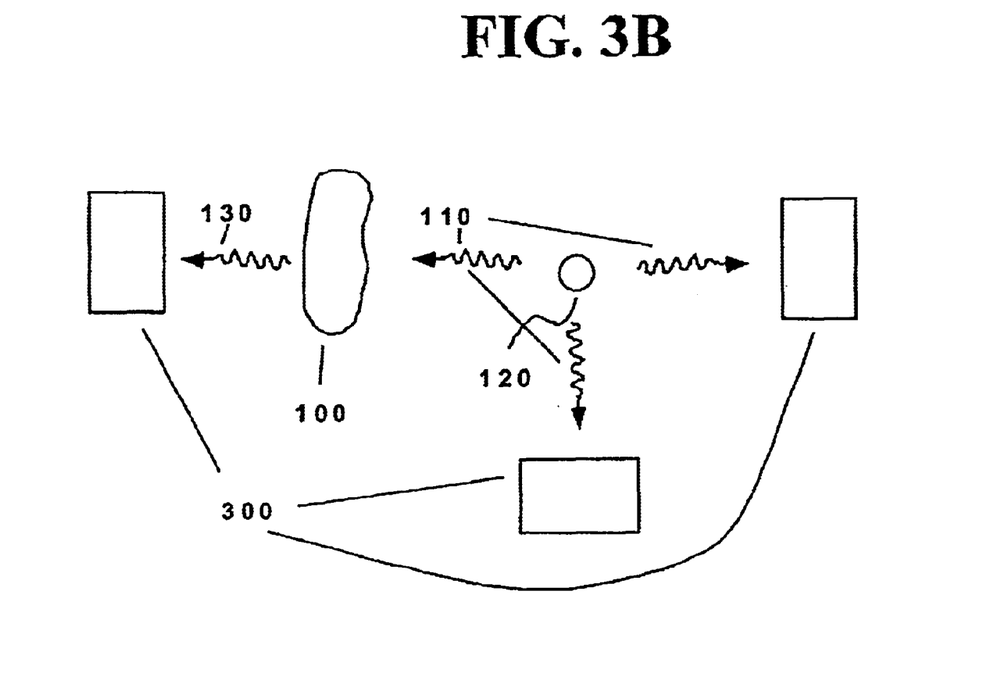
FIG. 3B is a simplified schematic illustration of another embodiment of the present invention whereby the radiation is transmitted to more than one spectrometer.

An incident beam of radiation 110 comprising neutrons is transmitted from the source 120, through the material 100 to produce a transmitted beam of radiation 130, to the spectrometer 300. The spectrometer 300 thermalizes and absorbs a portion of the transmitted beam 130 of neutrons as a function of location in the spectrometer 300, and produces a first thermal neutron intensity distribution in the spectrometer 300. If the source 120 further comprises a gamma ray source, the spectrometer 300 absorbs a portion of the transmitted beam 130 of gamma rays as a function of location in the spectrometer 300, and produces a first attenuated gamma ray intensity distribution in the spectrometer 300. The material 100 may also be removed so that a "blank" second thermal neutron intensity distribution (and second attenuated gamma ray intensity distribution) is produced in the spectrometer 300 for such purposes as calibration, baselining, and verification. In another embodiment of the present invention, shown in FIG. 3B, the material 100, does not need to be removed to obtain such "blank" intensity information.

Figure 4A:
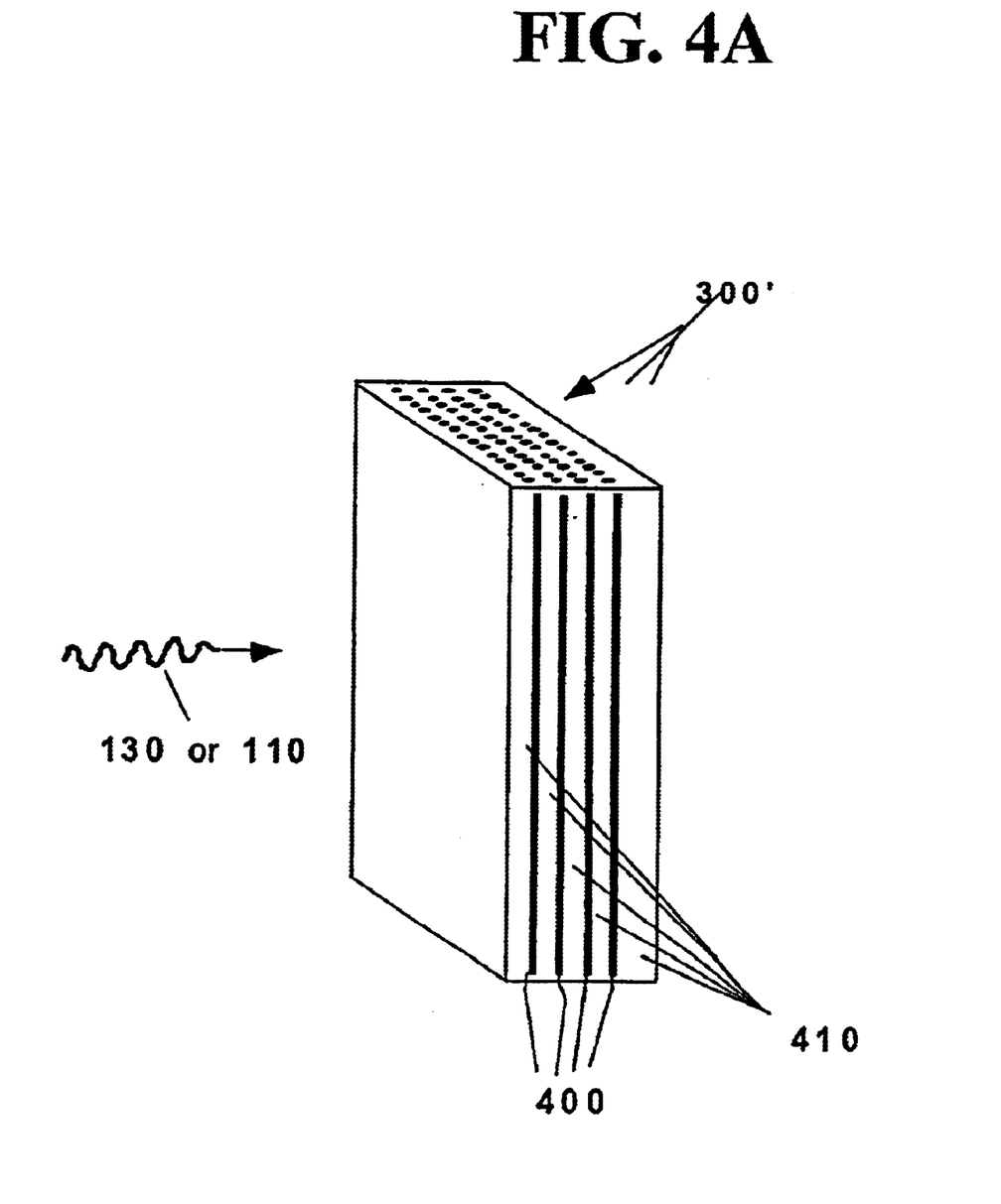
FIG. 4A is an illustration of a planar configuration of the moderating neutron spectrometer.
Figure 4B:
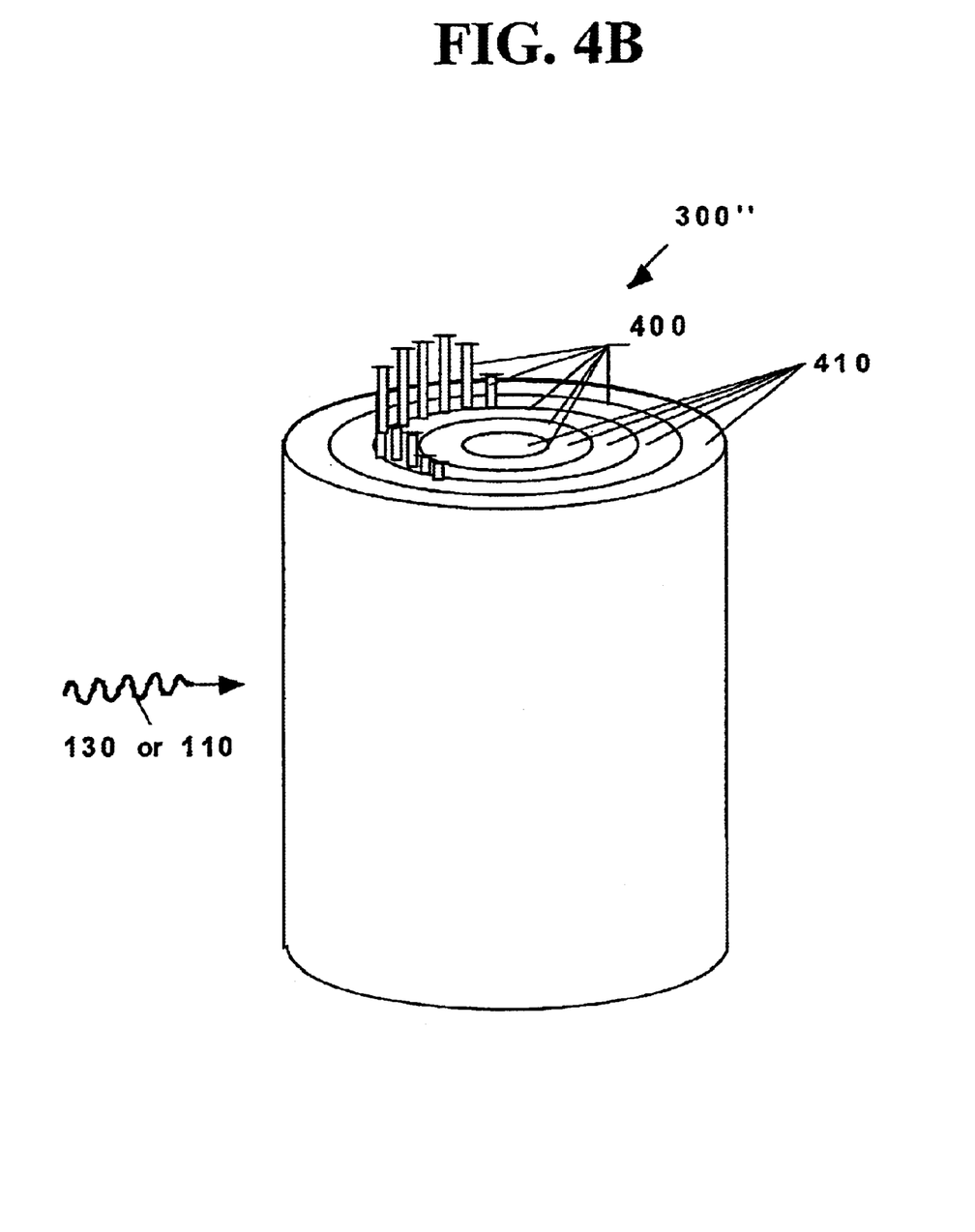
FIG. 4B is an illustration of a cylindrical configuration of the moderating neutron spectrometer.
Figure 4C:
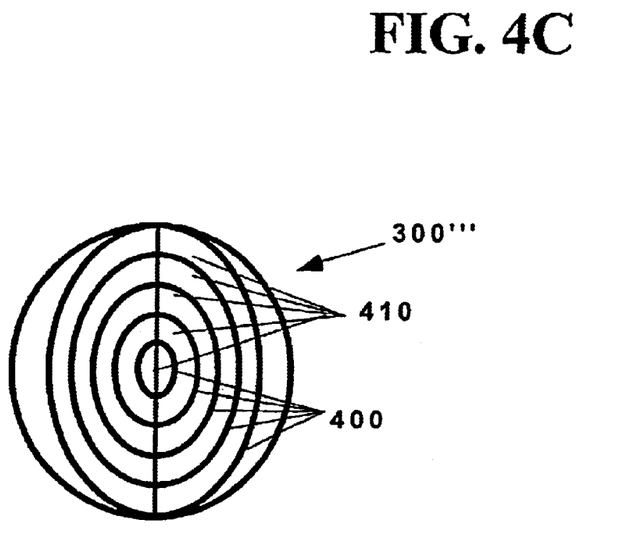
FIG. 4C is an illustration of a spherical configuration of the moderating neutron spectrometer.
Figure 4D:
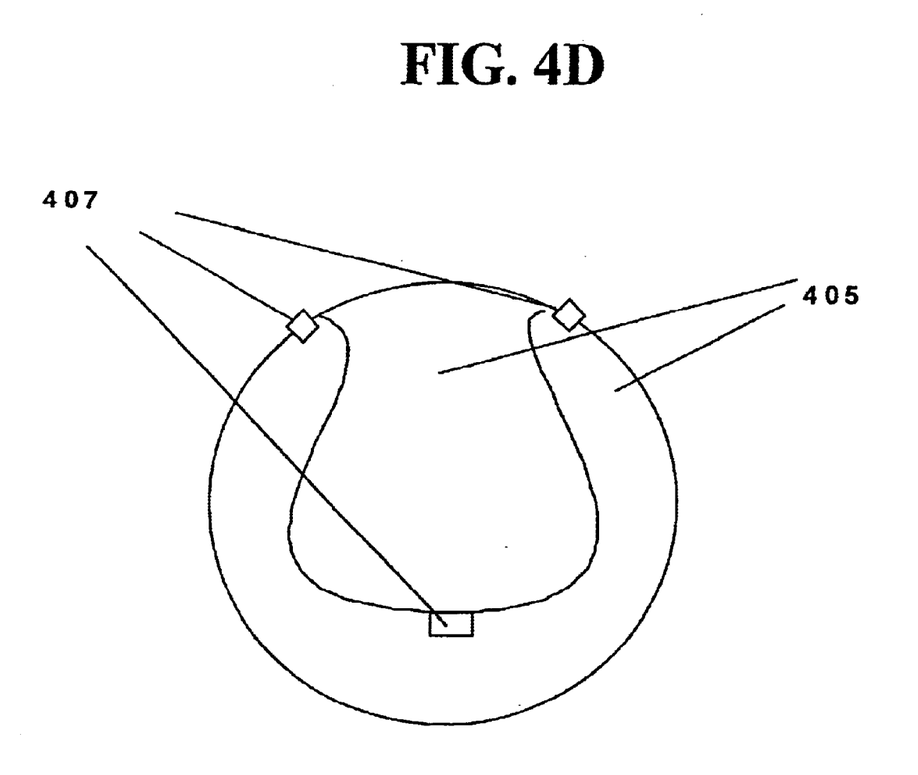
FIG. 4D is an illustration of a possible implementation of the spherical configuration of the moderating neutron spectrometer.

FIGS. 4A–4C illustrate examples of spectrometer 300 designs representing layered planar, cylindrical, and spherical configurations (300', 300", 300''', respectively). In each of these configurations, a first set (and any "blank" second set) of thermal neutron intensities at a plurality of locations in the moderator 410 of the spectrometer 300 is measured with a plurality of radiation detectors 400. Details of some possible implementations of the planar configuration using glass-fiber scintillators have been described elsewhere (e.g., "Glass-fiber-based neutron detectors for high- and low-flux environments," Mary Bliss, et al. in *Photoelectronic Detectors, Cameras, and Systems*, C. Bruce Johnson, Ervin, J. Fenyves, Editors, Proc. SPIE 2551,108–117,1995)— alternative planar configurations will be apparent to those skilled in the art. Because the cylindrical configuration is topologically equivalent to the planar configuration, means for implementation of the cylindrical configuration will also be apparent to those skilled in the art. Furthermore, it will be apparent to those skilled in the art, that a spherical configuration cannot be derived from a planar configuration. A close approximation to a spherical configuration which will provide an approximately spherically symmetric efficiency, however, can be achieved using scintillating fibers. FIG. 4D shows one mode of fabricating the layers comprising the radiation detectors 400 in the spherically symmetric structure of FIG. 4C. This mode is similar to that used in the manufacturer of baseballs whereby in the present invention each layer comprises two assembled scintillating fiber structures 405 (e.g., scintillating glass-fiber ribbons) whereby each structure 405 terminates with photomultipliers 407 to measure radiation counts.

Though FIGS. 4A–4C may be interpreted as representing evenly-spaced layers of radiation detectors 400 and continuous or near-continuous series of radiation detectors 400 within a layer, the present invention is not limited to such configurations. The optimum density or spacing of such radiation detectors 400 within each layer can be determined by mathematical computation or analytical modeling such as Monte Carlo N-Particle (MCNP) to meet the requirements of a specific application. Furthermore, the number and spacing of layers of radiation detectors 400 in the moderator 410 can be similarly determined. The radiation detectors 400 in FIGS. 4A–4B are exemplified using scintillating optical fibers (photodetectors and electronics not shown) arranged in layers though other geometric configurations could be used and with other types of radiation detectors 400 (e.g., B-10 fluoride tubes, He-3 tubes, and other types of ionization chambers). Alternative forms of scintillating materials include ribbon and sheet. The scintillating material may be organic, inorganic, lithium silicate glass, or plastic such as that sold by Bicron and is typically enriched with at least one neutron-reacting isotope (e.g., Li-6 and B-10 are commonly used). The moderator 410 is made of a material having neutron moderating properties such as graphite or a hydrogenous material, such as water (in gaseous, liquid, and solid forms), polyethylene (or other polyolefin), or combinations thereof. Furthermore, the moderator 410 may further comprise other materials that have particular neutron absorbing properties that provide further compositional information or improved spectrometer efficiency. For example, boron may be used to increase the neutron attenuation.

If the source 120 further comprises gamma rays, at least one first (and any "blank") attenuated gamma ray intensity in the moderator 410 of the spectrometer 300 is measured by at least one of the radiation detectors 400. As is known to those skilled in the art, the at least one radiation detector may comprise an ionization chamber or a scintillating material coupled to a photodetector such as a photomultiplier tube. The thermal neutron and gamma ray intensities may be simultaneously measured using radiation detectors 400 that are capable of distinguishing between thermal neutrons and gamma rays. In most circumstances, the required number of gamma ray intensity measurements is less than the number of thermal neutron measurements since the spectrometer 300 is typically designed to thermalize and absorb neutrons and not to significantly absorb gamma rays (the material 100 typically will be more effective than the spectrometer 300 in absorbing gamma rays). However, another embodiment of the present invention has the moderator 410 further comprising other materials that have particular gamma ray absorbing properties to provide further compositional information or improved spectrometer efficiency. For example, lead may be used to increase the gamma ray attenuation.

Figure 5A:
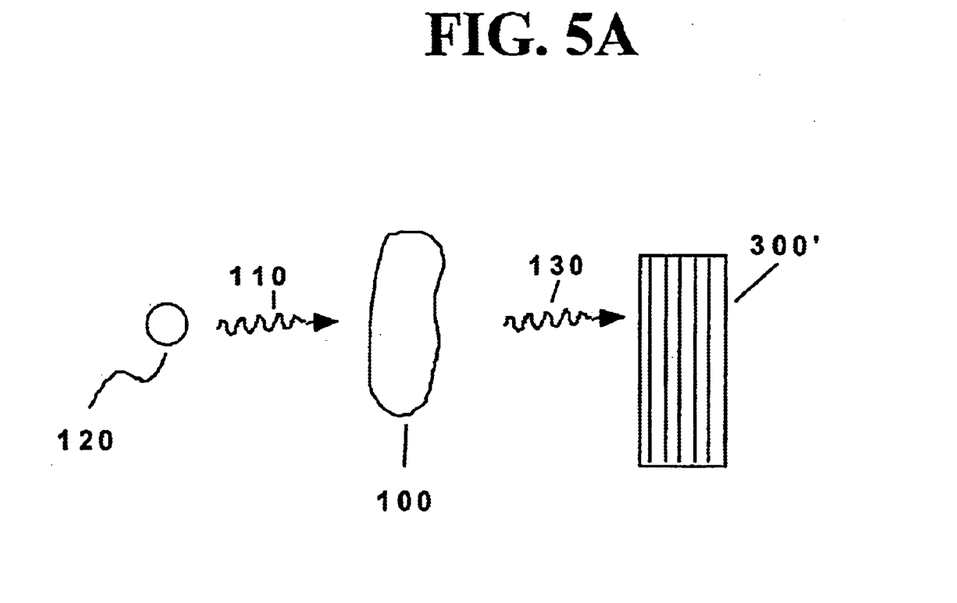
FIG. 5A illustrates an example of a transmission-type of application using a layered planar spectrometer.
Figure 5B:
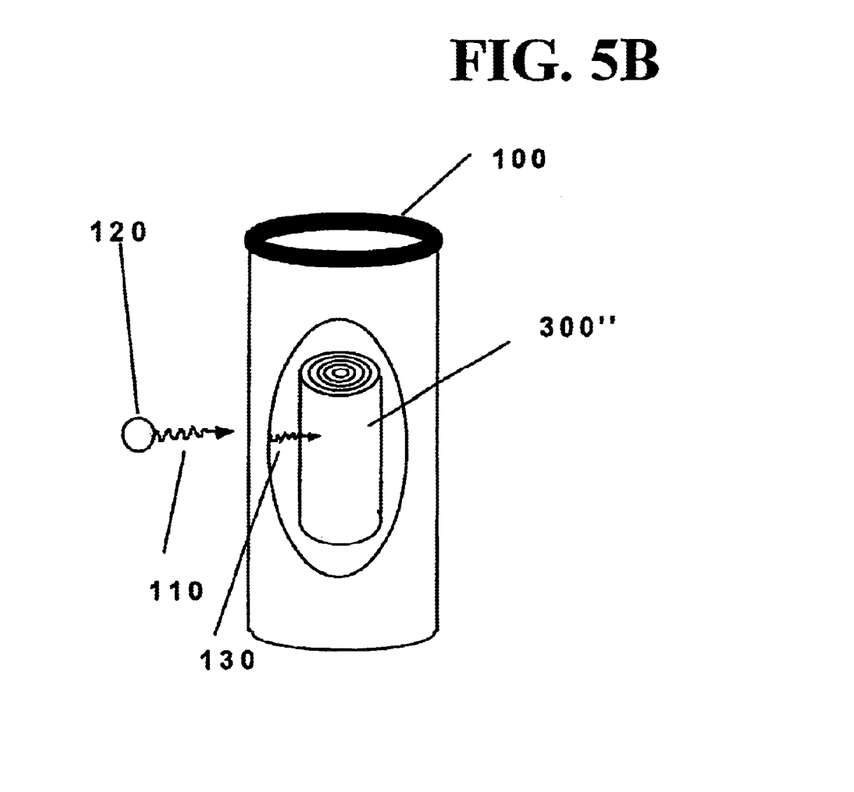
FIG. 5B illustrates an example of a transmission-type of application using a layered cylindrical spectrometer in a steam pipe or borehole and an external source.

The spectrometer 300 with the configurations shown in FIGS. 4A–4B is typically oriented in relation to the source 120 and/or material 100 such that the outputs from the individual radiation detectors 400 in a single layer are aggregated to improve sensitivity and accuracy in the composition measurement. FIGS. 5A–5B illustrate such embodiments for planar and cylindrical configurations, respectively.

One method by which the amount of hydrogen or hydrogen-bearing constituent of the material 100 is quantified is by comparing the measured first set (or first and second sets for improved accuracy) of thermal neutron intensities to a model to quantify the hydrogen-bearing constituent. The model may be analytical such as one that can be developed using MCNP or empirical, based on measurements made on test spectrometers. The amount of hydrogen or hydrogen-bearing constituent of the material 100 may also be quantified by comparing the measured first set (or first and second sets for improved accuracy) of thermal neutron intensities obtained from the material 100 with that obtained from a set of composition standards (e.g., by replacing the material 100 with the set of composition standards, radiating the standards, and measuring the thermal neutron (or thermal neutron and gamma ray) intensities under the same conditions). It will be apparent to those skilled in the art of measurement that there are alternative methods by which the amount of hydrogen or hydrogen-bearing constituent of the material 100 may be quantified. One such alternative method is by performing a sequence of measurements such as sequentially adding quantities of material 100 between the source 120 and spectrometer 300 while comparing the measured sets to the appropriate standards.

Figure 6A:
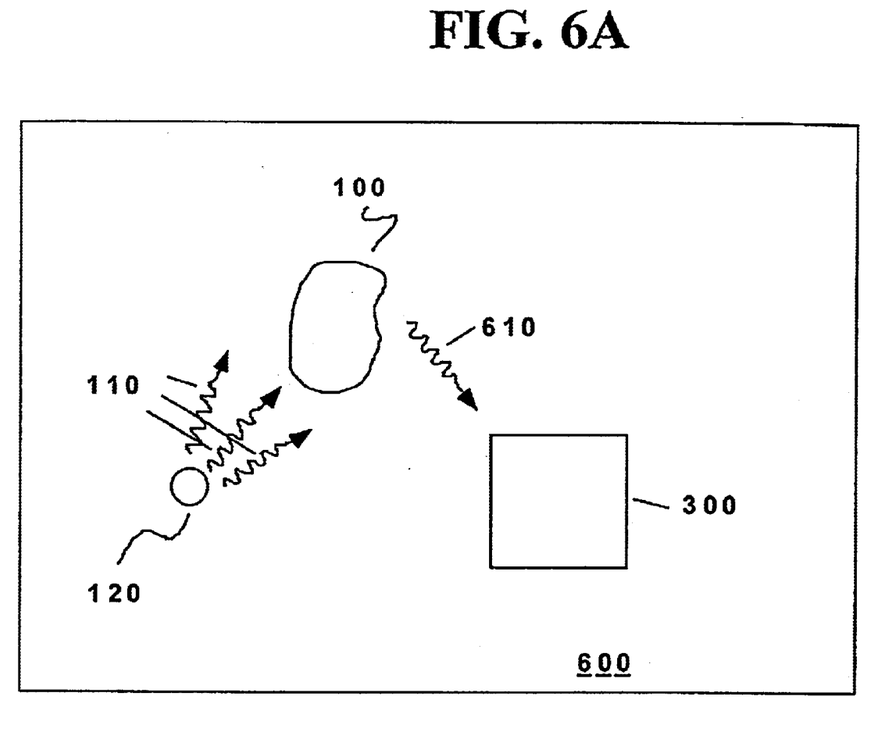
FIG. 6A is a simplified schematic illustration of another embodiment of the present invention whereby the radiation is backscattered from the material and its environment to the spectrometer.
Figure 6B:
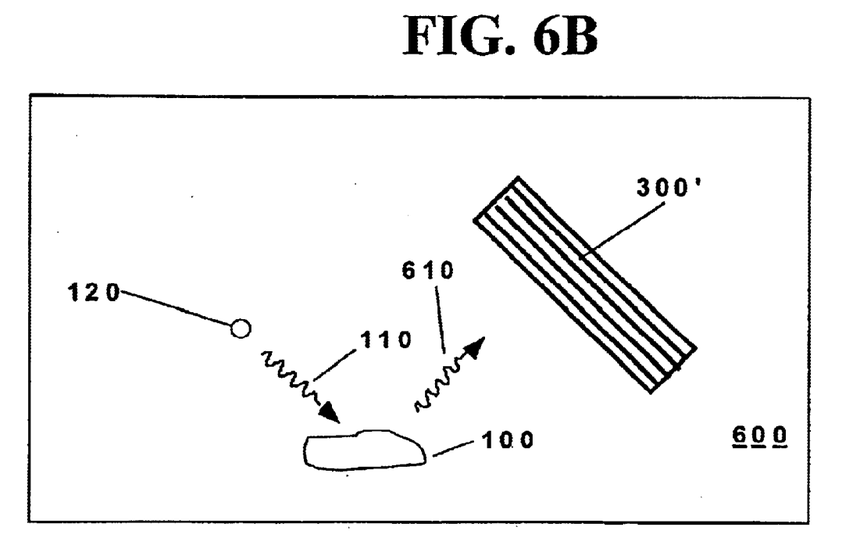
FIG. 6B illustrates an example of a backscattered-type of application using a planar spectrometer.
Figure 6C:
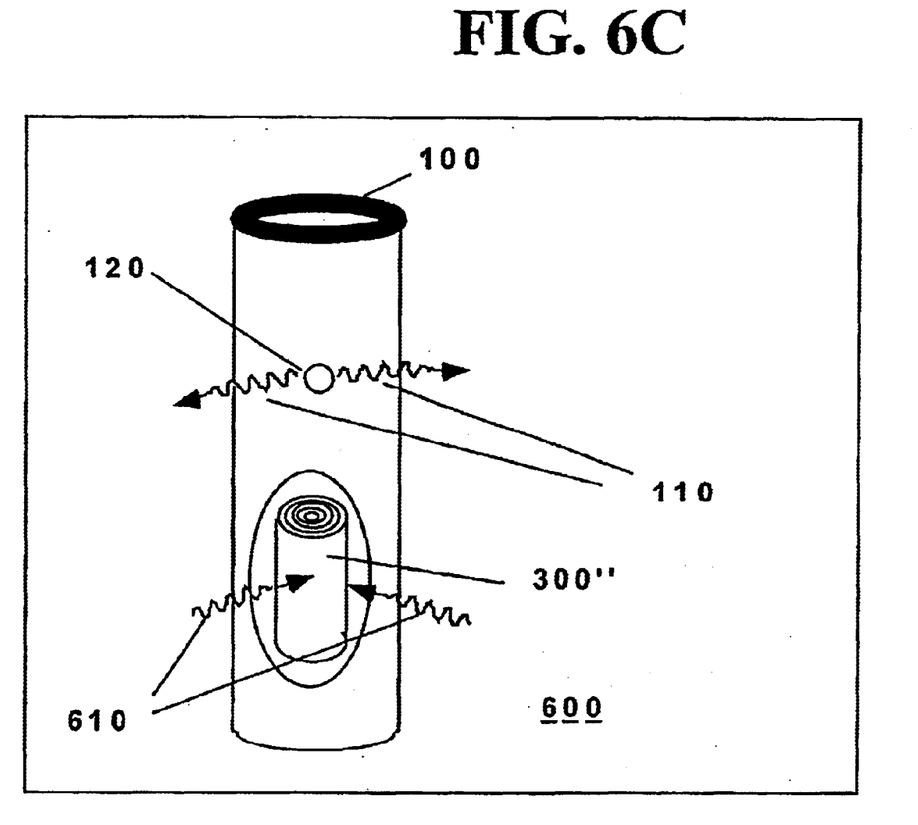
FIG. 6C illustrates an example of a backscattered-type of application using a cylindrical spectrometer in a steam pipe or borehole and an internal source.

In all of the embodiments thus far disclosed, the incident beam of radiation 110 is transmitted through the material 100 whereby the transmitted beam of radiation 130 is analyzed. In another embodiment of the present invention, shown in FIG. 6A, the material 100 is positioned in an environment 600 and an incident beam of radiation 110 comprising neutrons from a source 120 is transmitted to the material 100 and to the environment 600. The material 100 and environment 600 then backscatters a portion of the incident beam of radiation 610 to the moderating neutron spectrometer 300. The measured thermal neutron intensities are analyzed in a similar manner as the previously disclosed embodiments based on transmission. FIGS. 6B–6C illustrate two examples of a backscattered-type of application using a planar spectrometer and a cylindrical spectrometer in a steam pipe or borehole and an internal source, respectively.

Two examples of the steps in quantifying the amount of hydrogen or hydrogen-bearing constituent are provided below:

EXAMPLE 1

Comparison-of-forwards Technique

Step 1. Perform a "blank" neutron and gamma-ray count measurement by measuring counts without the material 100 in place to assure that the neutron spectrum emanating from the source 120 is within acceptable limits. Measure the number of neutron counts and number of gamma-ray counts in a fixed time period in each layer or for a fixed number of counts (in a specific layer or in total). Compare blank spectrum with an archived spectrum. If not within acceptable limits, recalibrate system;

Step 2. Place a composition standard between the source 120 and the spectrometer 300 to determine "standard" neutron and gamma-ray count. Measure the number of neutron counts and number of gamma-ray counts in a fixed time period or for a fixed number of counts (in a specific layer or in total). Repeat as necessary with different composition standards and possible interpolation/extrapolation utilizing one or more models;

Step 3. Place the material 100 between the source 120 and the spectrometer 300 to determine "material" neutron and gamma-ray counts. Measure number of neutron counts and number of gamma-ray counts in a fixed time period or for a fixed number of counts (in a specific layer or in total); and Step 4. Compare "material" and "standard" counts for each category (neutron, gamma-ray) and for each layer using statistical comparison methods (e.g., chi-squared, chi-squared-like techniques) to determine the probability that the composition is a certain value. Gamma-ray attenuation measurements can be utilized in conventional techniques to determine the thickness of the material 100, thus eliminating the need for the material 100 to have a standard length or thickness.

EXAMPLE 2

Overdetermination Technique

Step 1. Perform a "blank" neutron and gamma-ray count measurement by measuring counts without the material 100 in place to assure that the neutron spectrum from the source 120 is within acceptable limits. Measure the number of neutron counts and number of gamma-ray counts in a fixed time period in each layer or for a fixed number of counts (in a specific layer or in total). Compare blank spectrum with an archived spectrum. If not within acceptable limits, recalibrate system;

Step 2. Place the material 100 between the source 120 and the spectrometer 300 to determine "material" neutron and gamma-ray count. Measure the number of neutron counts and number of gamma-ray counts in a fixed time period or for a fixed number of counts (in a specific layer or in total); and Step 3. Invert overdetermined functions to determine material 100 thickness and composition using the methods of Bayesian statistics as taught by Bretthorst (G. Larry Bretthorst "Bayesian Spectrum Analysis and Parameter Estimation; Lecture Notes in Statistics, Vol 48, Springer 1989) or similar means.

In one application of the present invention, it can be used to measure the hydrogen content of meat or meat products. The hydrogen content of meat is widely used as a surrogate for the fat content. This is the underlying physical basis for multicolor x-ray techniques, however, neutrons are many times better than x-rays, both in contrast and penetrating power.

In another application of the present invention, it can be used to measure the hydrogen content of milk. Taken together with other information, such as the known chemical and physical properties of butterfats, the fat content of the milk can be obtained.

In another application of the present invention, it can be used to measure the quality of steam. At any given temperature below the critical temperature, water can coexist as a mix of vapor and condensed water. The heat content of the steam, which is a direct measure of its economic value, is smaller the "wetter" the steam, i.e., the greater the condensed water fraction. Measuring the hydrogen content of steam is a surrogate for measuring the density of the steam; taken with the temperature, the steam quality can be calculated.

In another application of the present invention, it can be used to improve well-logging operations commonly performed in the petroleum industry. In these measurements, as presently done, a neutron source or accelerator-based neutron generator is used to release neutrons into the material around a well, typically with cylindrical symmetry. Also, typically, neutron detectors are located on a common axis with the source, some distance above and/or below the source. These detectors are, typically gas-proportional counter, filled with a gas most-sensitive to thermal neutrons but with reduced sensitivity to more energetic neutrons, typically He-3. Typically, half of the thermal neutron detectors are enclosed with cadmium to filter out thermal neutrons and detect only those neutrons with energies greater than the cadmium cutoff, i.e., epicadmium neutrons. The result is that half the neutron detectors sense thermal neutrons plus, with reduced efficiency, epicadmium neutrons, thereby giving a measure of the energy distribution of the neutrons detected. This energy distribution provides valuable information about the chemical content of the material surrounding the well. The reduced detection efficiency of the neutron detectors to epicadmium neutrons means that these must count much longer for equal quality of data. The present invention, in a cylindrical configuration, will provide more information about the energy distribution of returning neutrons and, in addition will have comparable detection efficiencies for a range of neutron energies, thereby improving data quality.

In another application of the present invention, it can be used to provide a noncontact measure of the hydrogen content in fuels and other hydrocarbons. For instance, natural gas is composed of a mix of alkanes and olefins. To the extent that the olefins are separated from the gas (because they have significant economic value greater than their fuel value), the fuel value of the gas is directly proportional to the hydrogen content.

In another application of the present invention, it can be used to provide a noncontact measure of the hydrogen content of grain, beans, or oil seeds—such as cottonseed or rapeseed (canola). Taken together with other measurements of, or independent knowledge of, the water content can give the oil content, or, alternatively, if the oil content is independently known, measurements taken with the present invention can give the moisture content.

In another application of the present invention, it can be used to provide a rapid, nonintrusive measurement of the hydrogen content of containers such as luggage and packages. Excessive hydrogen content, may be indicative that the contents contain explosives or contraband, thereby indicating the need for other measurements.

CLOSURE

While embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A non-destructive method for quantifying the content of a hydrogen-bearing constituent in a material, comprising the steps of:
    positioning said material between a source and a moderator;
    transmitting an incident beam of radiation comprising neutrons from said source, through said material to produce a transmitted beam of radiation, to said moderator;
    receiving said transmitted beam of radiation at said moderator, wherein said moderator thermalizes and absorbs a portion of said transmitted beam and produces a first thermal neutron intensity distribution in said moderator;
    measuring a first set of thermal neutron intensities at a plurality of locations in said moderator; and
    quantifying the hydrogen-bearing constituent of said material using said measured first set of thermal neutron intensities.

2. The method of claim 1, further comprising the steps of:
    removing said material;
    transmitting said incident beam of radiation from said source to said moderator;
    receiving said incident beam at said moderator, wherein said moderator thermalizes and absorbs a portion of said incident beam and produces a second thermal neutron intensity distribution in said moderator;
    measuring a second set of thermal neutron intensities at said plurality of locations in said moderator; and
    wherein said quantifying further uses said measured second set of thermal neutron intensities.

3. The method of claim 2, wherein said quantifying comprises comparing said measured first and second sets of thermal neutron intensities to a model to quantify the hydrogen-bearing constituent.

4. The method of claim 1, further comprising the step of calibrating said measured first set of thermal neutron intensities by using a set of composition standards and wherein said quantifying comprises comparing said measured first set of thermal neutron intensities obtained from said material with that obtained from said set of composition standards.

5. The method of claim 1, wherein said first set of thermal neutron intensities is measured using a plurality of radiation detectors at said plurality of locations in said moderator.

6. The method of claim 5, wherein said radiation detectors comprise a scintillating material.

7. The method of claim 6, wherein said scintillating material is in fiber-optic form.

8. The method of claim 6, wherein said scintillating material is organic.

9. The method of claim 6, wherein said scintillating material is inorganic.

10. The method of claim 9, wherein said scintillating material comprises lithium silicate glass.

11. The method of claim 6, wherein said scintillating material is enriched with at least one neutron-reacting isotope.

12. The method of claim 11, wherein said at least one neutron-reacting isotope is Lithium-6.

13. The method of claim 5, wherein said plurality of locations in said moderator form alternating layers of radiation detectors and moderator material.

14. The method of claim 13, wherein said alternating layers are in a planar configuration.

15. The method of claim 13, wherein said alternating layers are in a cylindrical configuration.

16. The method of claim 13, wherein said alternating layers are in a spherical configuration.

17. The method of claim 1, wherein said moderator is made of a moderator material that comprises hydrogen.

18. The method of claim 17, wherein said moderator material comprises a polyolefin.

19. The method of claim 1, wherein said source is selected from a fissionable isotope, an ($\alpha$,n) source, a neutron generator, and combinations thereof.

20. The method of claim 1, wherein said hydrogen-bearing constituent of said material is fat.

21. The method of claim 20, wherein said material is meat.

22. The method of claim 1, wherein said hydrogen-bearing constituent of said material is water.

23. The method of claim 22, wherein said material is steam.

24. A non-destructive method for quantifying the content of a hydrogen-bearing constituent in a material, comprising the steps of:
    positioning at least two moderating neutron spectrometers about a source such that said spectrometers are equidistant from said source;
    positioning said material between said source and at least one of said spectrometers;
    transmitting an incident beam of radiation comprising neutrons from said source to said spectrometers;
    receiving said incident beam at said spectrometers, wherein said spectrometers thermalize and absorb a portion of said incident beam and produce thermal neutron intensity distributions in said spectrometers;

measuring said thermal neutron intensities; and quantifying the hydrogen-bearing constituent of said material using said measured thermal neutron intensities.

25. A non-destructive method for quantifying the content of a hydrogen-bearing constituent in a material, comprising the steps of:

positioning said material proximate to a moderating neutron spectrometer;

transmitting a beam of radiation comprising neutrons from a source to said material wherein said spectrometer receives a portion of said beam of radiation that has interacted with said material;

measuring a first set of thermal neutron intensities in said spectrometer; and quantifying the hydrogen-bearing constituent of said material using said measured first set of thermal neutron intensities.

26. The method of claim 25, further comprising the steps of:

removing said material;

transmitting said beam of radiation from said source to said spectrometer;

measuring a second set of thermal neutron intensities in said spectrometer; and wherein said quantifying further uses said measured second set of thermal neutron intensities.

* * * * *